(12) United States Patent
Campbell et al.

(10) Patent No.: US 9,482,604 B2
(45) Date of Patent: Nov. 1, 2016

(54) EQUI-BIAXIAL MEMBRANE STRETCHER

(71) Applicant: Northeastern University, Boston, MA (US)

(72) Inventors: William Campbell, Boston, MA (US);
Michael Howard, Boston, MA (US);
Jarrett Shamlian, Boston, MA (US);
Kai-Tak Wan, Natick, MA (US)

(73) Assignee: NORTHEASTERN UNIVERSITY, Boston, MA (US)

( * ) Notice: Subject to any disclaimer, the term of this patent is extended or adjusted under 35 U.S.C. 154(b) by 0 days.

(21) Appl. No.: 14/394,488

(22) PCT Filed: Apr. 17, 2013

(86) PCT No.: PCT/US2013/036995
§ 371 (c)(1),
(2) Date: Oct. 15, 2014

(87) PCT Pub. No.: WO2013/158774
PCT Pub. Date: Oct. 24, 2013

(65) Prior Publication Data
US 2015/0101418 A1    Apr. 16, 2015

Related U.S. Application Data

(60) Provisional application No. 61/625,466, filed on Apr. 17, 2012.

(51) Int. Cl.
*G01N 3/08* (2006.01)
(52) U.S. Cl.
CPC ......... *G01N 3/08* (2013.01); *G01N 2203/0254* (2013.01); *G01N 2203/0282* (2013.01); *G01N 2203/0435* (2013.01)

(58) Field of Classification Search
CPC ............. G01N 2203/0254; G01N 2203/0282; G01L 1/205
USPC ........... 73/831, 826, 856, 862, 393, 862.393
See application file for complete search history.

(56) References Cited

U.S. PATENT DOCUMENTS 4,291,454 A * 9/1981 Sawaryn ................. B25B 27/28
29/235
4,516,882 A * 5/1985 Brewer ................. B63B 21/502
114/265

(Continued)

FOREIGN PATENT DOCUMENTS

JP    11-214487 A    8/1999

OTHER PUBLICATIONS

No Author Listed, "*Biaxial Planar Testing of Soft Tissues*," Instron. com. Downloaded from http://72.3.156.133/wa/solutions/Soft_Tissues_Biaxial_Planar_Testing.aspx on Jul. 15, 2015 (1 pg.).

(Continued)

*Primary Examiner* — Max Noori

(57) ABSTRACT

A system for and method of stretching a membrane is provided. The system has a top plate and a bottom plate that are in parallel with each other and a plurality of flexible v trusses. The top plate is configured to move vertically. The v trusses are placed in circle and have arms pointing to the center. There is a clamp for each arm for clamping a membrane. When external force is applied to push the top plate towards the bottom plate, the force bends the trusses, which is translated to the horizontal displacement of the trusses with arms. As the trusses move outwards, the clamped membrane is stretched.

19 Claims, 8 Drawing Sheets

(56) References Cited

U.S. PATENT DOCUMENTS

| | | | |
|---|---|---|---|
| 4,685,230 A | | 8/1987 | Mason, III |
| 5,448,918 A | * | 9/1995 | Tucchio .................. G01N 3/04 |
| | | | 73/818 |
| 5,882,353 A | | 3/1999 | VanBeek et al. |
| 5,885,501 A | | 3/1999 | Gardner et al. |
| 6,057,150 A | | 5/2000 | Lee et al. |
| 6,868,156 B1 | * | 3/2005 | Narayan .................. H04Q 1/30 |
| | | | 379/379 |
| 7,204,160 B1 | | 4/2007 | Sadegh et al. |
| 8,882,644 B2 | * | 11/2014 | Jahns ................. A63B 21/0004 |
| | | | 482/111 |
| 2004/0092977 A1 | * | 5/2004 | Vargas .................. A61B 17/11 |
| | | | 606/155 |
| 2005/0037904 A1 | * | 2/2005 | Chang ............. A63B 21/00043 |
| | | | 482/122 |
| 2005/0182480 A1 | * | 8/2005 | Doran ....................... A61F 2/91 |
| | | | 623/1.15 |
| 2006/0279721 A1 | | 12/2006 | Baggen et al. |
| 2008/0269873 A1 | * | 10/2008 | Israel ........................ A61F 2/91 |
| | | | 623/1.16 |
| 2009/0137371 A1 | * | 5/2009 | Fuller ................ A63B 21/0552 |
| | | | 482/122 |
| 2010/0292054 A1 | * | 11/2010 | Karpus ............. A63B 21/0004 |
| | | | 482/122 |
| 2011/0200702 A1 | | 8/2011 | Harada et al. |

OTHER PUBLICATIONS

"ADMET—Biaxial Testing Machines," Universal Materials Testing Machines https://web.archive.org/web/20110908145023/http://www.admet.com/biaxial_testing_machines.htm as Downloaded on Jun. 2, 2015 (1 pg.).

"Specifications." AccuPull. Inventure Labs. Downloaded from https://web.archive.org/web/20130813212917/http://accupull.com/specifications.html on Jun. 2, 2015 (1 pg.).

"*InterstatePlastics—Materials*." Interstate_Plastics.com Website. Downloaded from http://www.interstateplastics.com/materials.php on Jun. 2, 2015 (2 pgs.).

International Search Report and Written Opinion issued by the U.S. Patent and Trademark Office as International Searching Authority for International Application No. PCT/US2013/036995 mailed Jul. 22, 2013 (7 pgs.).

Brieu, et al., "A New Biaxial Tension Test Fixture for Uniaxial Testing Machine—a Validation for Hyperelastic Behavior of Rubber-Like Materials," Journal of Testing and Evaluation, vol. 35, No. 4, Paper ID JTE100688, pp. 1-9 (Jul. 2007).

Budynas, et al., *Shigley's Mechanical Engineering Design*. New York: McGraw-Hill, 2011—Title Page and Table of Contents only (Total 9 pgs.).

Ganesan et al., "Effect of Nitrogen Doping on the Mechanical Properties of Carbon Nanotubes," ACS Nano, vol. 4 (12), pp. 7637-7643 (2010).

Billiar, K. and Sacks, M.S., "A Method to Quantify the Fiber Kinematics of Planar Tissues under Biaxial Stretch," Journal of Biomechanics, vol. 30(7), pp. 753-756 (1997).

Hitt, et al., "Development of a Machine for the Stretching of Polymers" Polymer Testing, vol. 19 pp. 27-41 (2000).

* cited by examiner

EQUI-BIAXIAL MEMBRANE STRETCHER

CROSS-REFERENCE TO RELATED APPLICATIONS

This application is a National Stage Entry of PCT International Application No. PCT/US2013/36995 filed Apr. 17, 2013, entitled "Equi-Biaxial Membrane Stretcher," which claims priority to U.S. Provisional Application No. 61/625,466 entitled "Equi-bixial Stretcher of a Thin Membrane," filed on Apr. 17, 2012, the contents of which is incorporated herein by reference in their entirety.

BACKGROUND

1. Field of the Invention

The present disclosure relates to the field of membrane stretcher and specifically to the field of equi-biaxial membrane stretcher.

2. Description of Related Art

Characterization of the material properties of thin membranes is needed for important research in the biomechanical field. Stretching of a thin membrane is crucial in the biomedical and biomechanical fields because organic materials have naturally varying material properties. Likewise for newly developed prosthetic and synthetic materials, one way to learn about their material properties is through analyzing empirical data gathered from testing. Stretching can provide researchers with a quantitative knowledge of the elastic and failure properties of thin membranes, such as contact lenses. Improved characterization will allow for many improvements in the understanding of thin soft membranes such as lenses, skin, and artificial tissues.

Various human tissues and membranes experience loading conditions in the body that are not duplicated well during out-of-the-body testing. These tissues are anisotropic, meaning they respond differently depending on the direction of the force applied. While in the body, they are subject to an equi-biaxial load, meaning they are stretched equally along the circumference if sample is circular.

Many organic membranes, notably cornea lenses and the walls of heart valves, naturally undergo equi-biaxial loading. The current methods for putting a thin membrane under biaxial load only stretch the sample in two perpendicular directions, falling short of truly simulating natural equi-biaxial loading. While under the equi-biaxial load, researchers can inspect the sample with a microscope or subject it to various probing and indenting techniques to determine its mechanical properties. The properties of these membranes need to be better understood so organic replacement parts can be engineered.

Current commercial technology and equipment for testing the physical properties of thin membranes is extremely expensive (close to $200,000), cumbersome, and sometimes limited in capability and flexibility. There remains a need for a technology and/or equipment that is more synergistic and versatile and yet affordable.

SUMMARY OF THE INVENTION

An equi-biaxial stretcher for stretching a membrane is provided. The stretcher can be used for testing thin organic membranes in order to characterize their material and mechanical properties. The stretcher uses one vertical load to stretch the membrane in radial directions. The system uses angled trusses to translate a vertical load into radial displacement. The stretcher includes clamps to hold and pull a sample membrane. The top and bottom portions of the clamps can be made separable and can clip onto each other.

In an aspect of the present disclosure, a system for stretching a membrane is provided. The system includes a first main plate configured to receive force perpendicular to a surface of the first main plate and move perpendicular to the surface and a second main plate substantially in parallel with the first main plate. The system also includes a plurality of trusses evenly distributed in circle, each truss comprising two legs and an arm. The at least two legs and the arm meet at a center of their corresponding truss. The two legs meet at a first angle less than 180 degrees. A first leg of the at least two legs of each truss is coupled to the first main plate, and a second leg of the at least two legs of each truss is coupled to the second main plate. The arm of each truss points in a radially inward direction, and the center of each truss points in a radially outward direction. The system also includes a plurality of clamps, each clamp coupled to an end of a corresponding arm of a truss in the plurality of trusses for clamping a membrane. Moving the first main plate towards the second main plate causes the plurality of trusses to bend such that the at least two legs of each truss meet at a second angle less than the first angle to stretch the clamped membrane.

In another aspect of the present disclosure, a method of stretching a membrane using a membrane stretcher is provided. The method includes providing a membrane, clamping a membrane with the plurality of clamps of the above system, and applying force substantially vertical to the first main plate for stretching the membrane.

In a further aspect of the present disclosure, a method of using a membrane stretcher is provided. The method includes inserting an insertable stage into the membrane stretcher with separable top and bottom portions, and raising the insertable stage to substantially level with the plurality of arms. The method also includes placing the bottom clamp portions of the plurality of clamps on the insertable stage, placing a membrane on the bottom clamp portions, attaching the top clamp portions of the plurality of clamps to the bottom clamp portions, and lowering the insertable stage.

DETAILED DESCRIPTION OF THE INVENTION

Figure 1:
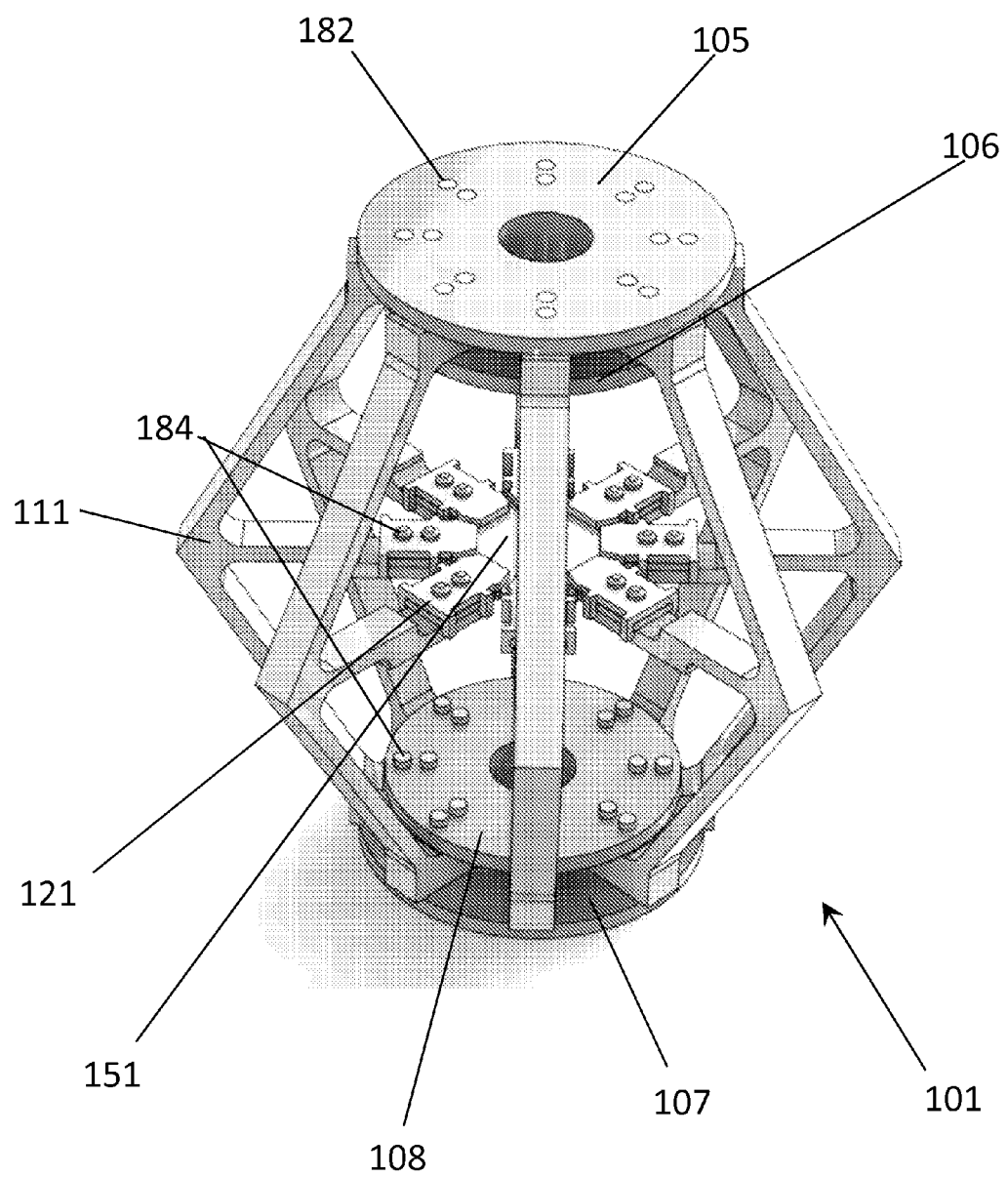
FIG. 1 illustrates an equi-biaxial stretcher in accordance with embodiments of the present disclosure.

In an aspect of the present disclosure, a system for stretching a membrane is provided. The system includes a first main plate configured to receive force perpendicular to a surface of the first main plate and move perpendicular to the surface and a second main plate substantially in parallel with the first main plate. The system also includes a plurality of trusses evenly distributed in circle, each truss comprising two legs and an arm. The at least two legs and the arm meet at a center of their corresponding truss. The two legs meet at a first angle less than 180 degrees. A first leg of the at least two legs of each truss is coupled to the first main plate, and a second leg of the at least two legs of each truss is coupled to the second main plate. The arm of each truss points in a radially inward direction, and the center of each truss points in a radially outward direction. The system also includes a plurality of clamps, each clamp coupled to an end of a corresponding arm of a truss in the plurality of trusses for clamping a membrane. Moving the first main plate towards the second main plate causes the plurality of trusses to bend such that the at least two legs of each truss meet at a second angle less than the first angle to stretch the clamped membrane.

In an embodiment, moving the first main plate towards the second main plate can exert substantially equal force to the plurality of trusses to displace each of the plurality of arms and the plurality of clamps in a radially outward direction.

In an embodiment, the system can also include a first secondary plate for fixing the first legs of the plurality of trusses between the first main plate and the first secondary plate and a second secondary plate for fixing the second legs of the plurality of trusses between the second main plate and the second secondary plate.

In another embodiment, the first and second secondary plates can be swappable. In a further embodiment, each arm can bisect an angle between the first and second legs of its corresponding truss, and the plurality of arms can be substantially parallel with the first and second main plates.

In another embodiment, the system can also include an insertable stage and a positioning column configured to lift the stage.

Other exemplary embodiments are also provided. The second main plate can have a hole for inserting a microscope for observing a membrane. Each clamp of the plurality of clamps can include a top clamp portion and a bottom clamp portion, the top clamp portion and the bottom clamp portion being separable. The plurality of trusses can include at least eight trusses and the plurality of clamps comprise at least eight clamps. The plurality of trusses can include at least one of polymers or metals. The plurality of trusses can be made by 3D printing. The plurality of trusses can be made by injection molding. The plurality of trusses can include a non-corrosive material. The non-corrosive material can include at least one of Delrin, UHMW, Nylon 6/6, Nylon 6/12, Teflon, PEEK, and PE.

In another aspect of the present disclosure, a method of stretching a membrane using a membrane stretcher is provided. The method includes providing a membrane, clamping a membrane with the plurality of clamps of the above system, and applying force substantially vertical to the first main plate for stretching the membrane.

In a further aspect of the present disclosure, a method of using a membrane stretcher is provided. The method includes inserting an insertable stage into the membrane stretcher with separable top and bottom portions, and raising the insertable stage to substantially level with the plurality of arms. The method also includes placing the bottom clamp portions of the plurality of clamps on the insertable stage, placing a membrane on the bottom clamp portions, attaching the top clamp portions of the plurality of clamps to the bottom clamp portions, and lowering the insertable stage.

In an embodiment, the top clamp portions can be placed on a top clamp holder and attaching the top clamp portions can include lowering the top clamp holder. In another embodiment, the method can include applying force substantially perpendicular to the first main plate for stretching the membrane. In yet another embodiment, the insertable stage is raised with a positioning column inserted through a hole in the second main plate. In a further embodiment, the method includes aligning the plurality of arms with the insertable stage. In another embodiment, the method includes inserting a microscope to observe the membrane.

Structure of Equi-Biaxial Stretcher

A system for and method of stretching a membrane is provided. The system includes top and bottom plates and trusses connecting the top and bottom plates. These inclined trusses are flexible trusses such that they can be bent when the top plate is pushed towards the bottom plate. The vertical force can be translated into a horizontal, radial displacement of the trusses. As a result, clamps clipping a membrane will be pulled and the membrane will be stretched.

To translate a vertical load to a horizontal load, the system can be designed based on Ganesan's device and using a beam theory. In a study performed on carbon nanotubes by Ganesan, a fixture was created to apply a vertical load and translate it to a horizontal load. (See Ganesan et al. "Effect of Nitrogen Doping on the Mechanical Properties of Carbon Nanotubes" ACS Nano 2010).

FIG. 1 shows an equi-biaxial stretcher 101 according to some embodiments. The equi-biaxial stretcher 101 includes a top plate 105, a bottom plate 107, and a number of v trusses 111. The v trusses 111 are connected to the top plate 105 and the bottom plate 107. To provide better attachment of the v trusses to the top and bottom plates, there can be a secondary top plate 106 and a secondary bottom plate 108. The top plate 105, the trusses 111, and the secondary top plate 106 and the bottom plate 107, the trusses 111, and the secondary bottom plate 108 can be connected using dowel pins 184. For connecting using dowel pins 184, the plates and the trusses can have dowel pin holes 182. The equi-biaxial stretcher 101 also has clamps 121 clamping and pulling a membrane 151. The equi-biaxial stretcher 101 in FIG. 1 has eight trusses 111. The stretcher 101 is a non-limiting example, and there can be other configurations. For example, another equi-biaxial stretcher may have a different number of trusses. The top and bottom plates and the trusses can be connected differently, or they can be manufactured in one part so that there is no need for connecting the elements together. Also, other stretchers may not include the secondary plates.

The trusses will displace and deflect as a vertical load is applied. These displacements and deflections can be accounted for by using linear elastic beam theory. The beam material used for this design can be a metal or high polymer plastic with a high modulus of elasticity to minimize deflection. Using plastic can be beneficial because of its non-corrosive characteristic when submerged in a saline solution as well as its capability of being sterilized. A strong material can be chosen to endure repeated loads.

All components can be machined, turned, or 3D printed in polymers that meet elastic deflection requirements. The components can also be made using injection molding. Alternatively, the plates can be printed in ABS plastic and fastened using 3 nylon screws per pair. The apparatus can be of any size and scalable, and in some embodiments, it can be built to fit within a 4-inch cube.

Figure 2:
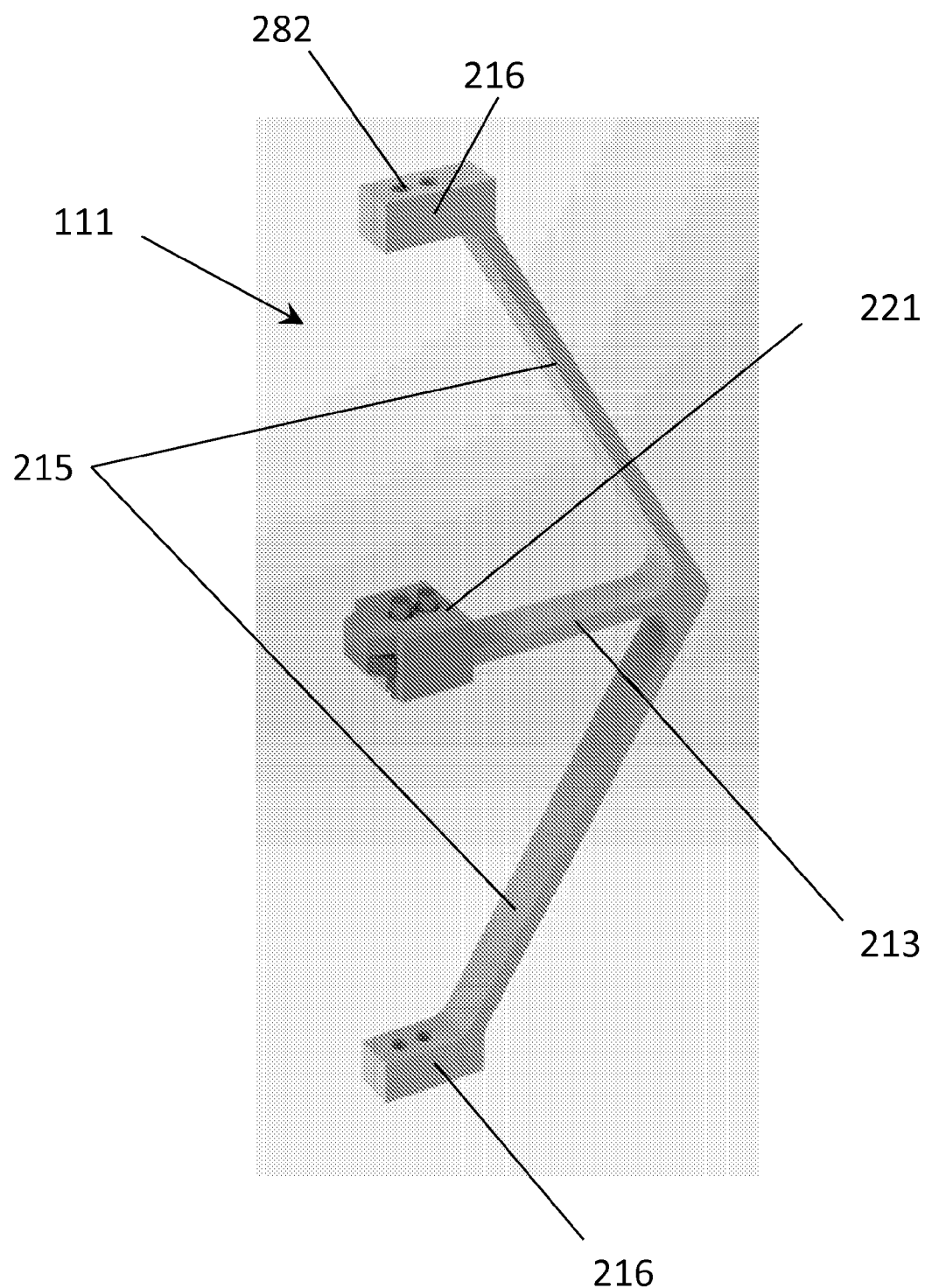
FIG. 2 illustrates a truss of an equi-biaxial stretcher in accordance with embodiments of the present disclosure.

The mechanism to hold a test membrane in place can be a simple mechanical clip. FIG. 2 shows an exemplary truss 111 and a clamp 221 according to some embodiments. The truss 111 has two legs 215 and an arm 213. In some embodiments, the lengths of the two legs 215 are identical. The two legs 215 meet at an angle less than 180 degrees and the arm 213 bisects this angle. The leg ends 216 can have dowel pin holes 282, which can be used to connect to the top and bottom plates. The clamp 221 is connected to the end of the arm. The arm and the clamp can also be connected with dowel pins. The clamps 221 can be a disposable clip that could be inexpensively produced using injection molding or 3D printing.

Figure 3A:
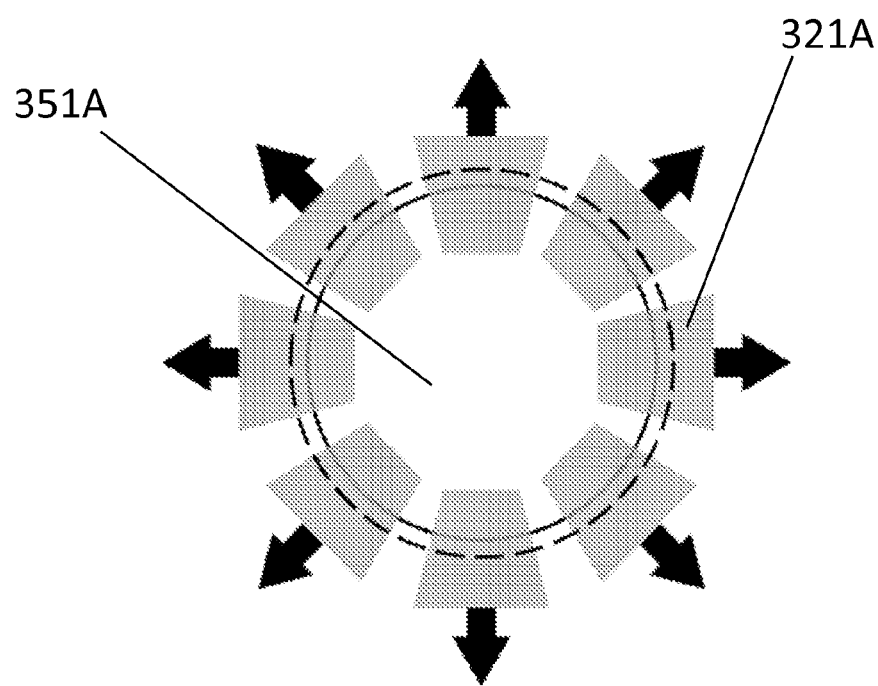
FIG. 3A illustrates an upper view of clamps of an equi-biaxial stretcher clamping a membrane in accordance with embodiments of the present disclosure.

FIG. 3A shows an upper view of clamps 321A clamping a membrane 351A. There are eight clamps that are placed evenly in circle. The clamps are configured to be displaced radially to stretch the membrane.

Figure 3B:
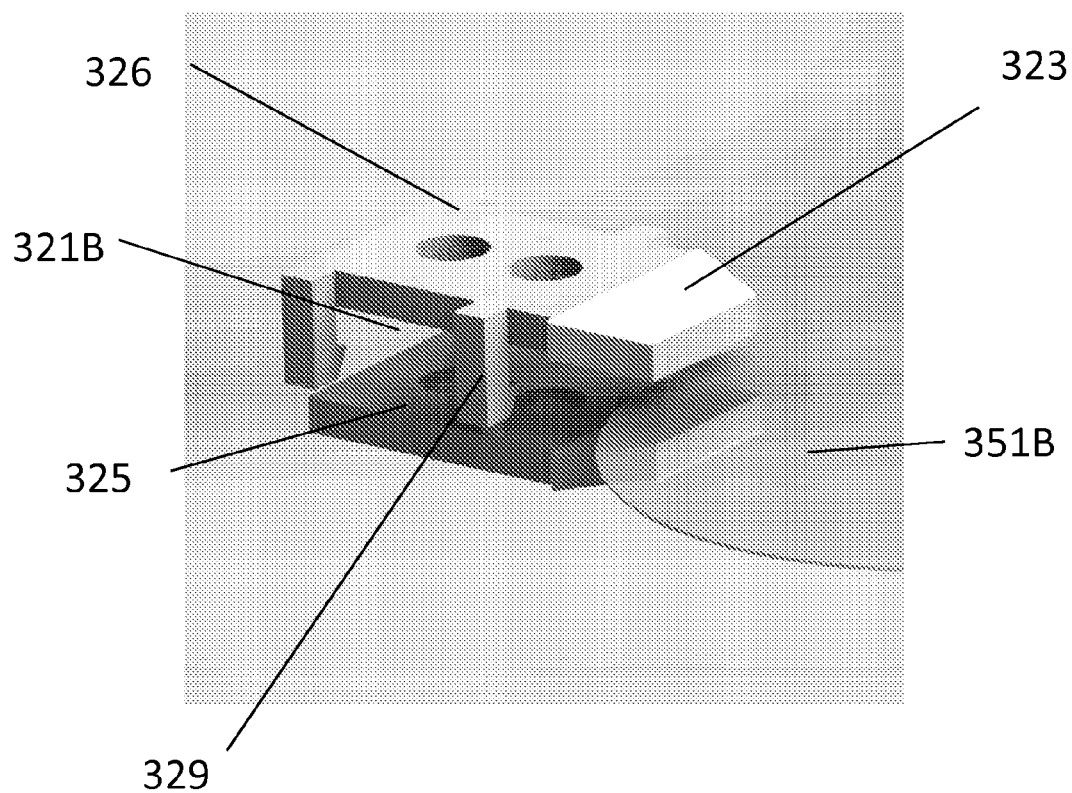
FIG. 3B illustrates a separable top and bottom portions of a clamp of an equi-biaxial stretcher in accordance with embodiments of the present disclosure.

FIG. 3B illustrates a clamp 321B of an equi-biaxial stretcher. The clamp can be made as one element or multiple elements that can be connected together. The clamp 321B has a separable bottom portion 325, a separable top portion 326, clipping elements 329, and clamping surfaces 323. The clipping elements 329 are connected to the top portion 326 and can clip onto the bottom portion 325. Alternatively, the clipping elements can be attached to the bottom portion and clip onto the top portion. Other configurations of attaching the top and bottom portions are also possible. The clamping surfaces 323 can be made to grip membranes firmly without tearing or deforming. The clamping surfaces can, for example, be flat, serrated flats, or rough, or can have rubber inserts.

The clamps can have various clamping angles for gripping samples of different thicknesses. As an example, the bottom portions have a different angle at which they rise to meet the top portions and grip membranes. Using optimal angles to grip membranes can reduce the damage to the membranes and can provide stronger grip.

Figure 4A:
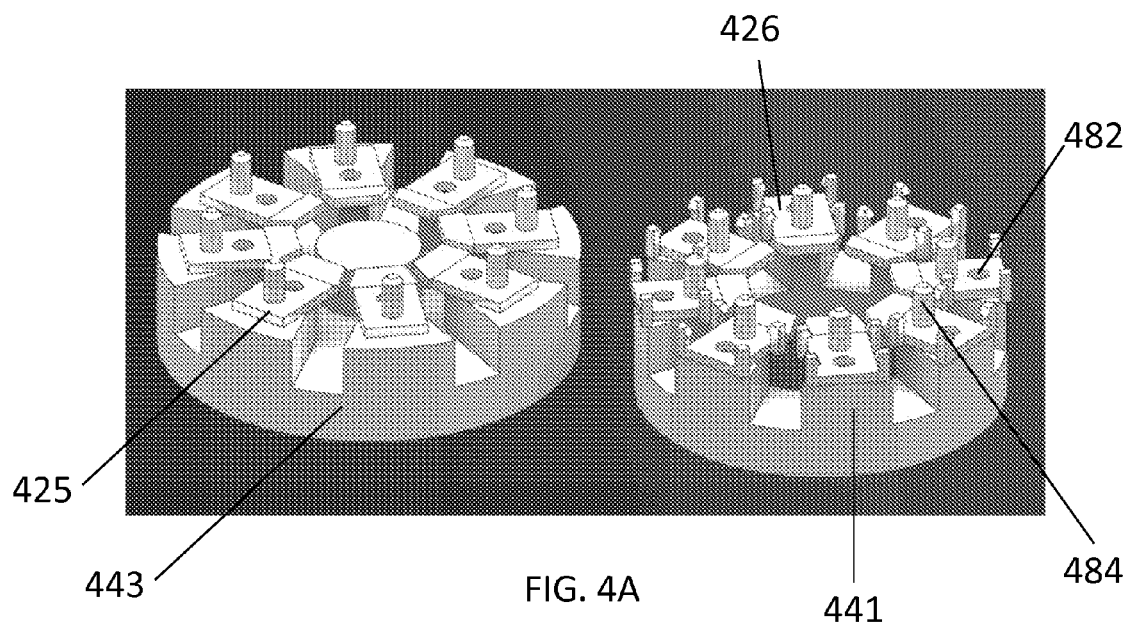
FIG. 4A illustrates an insertable stage with bottom portions of clamps and an insertable top clamp holder with top portions of clamps in accordance with embodiments of the present disclosure.
Figure 4B:
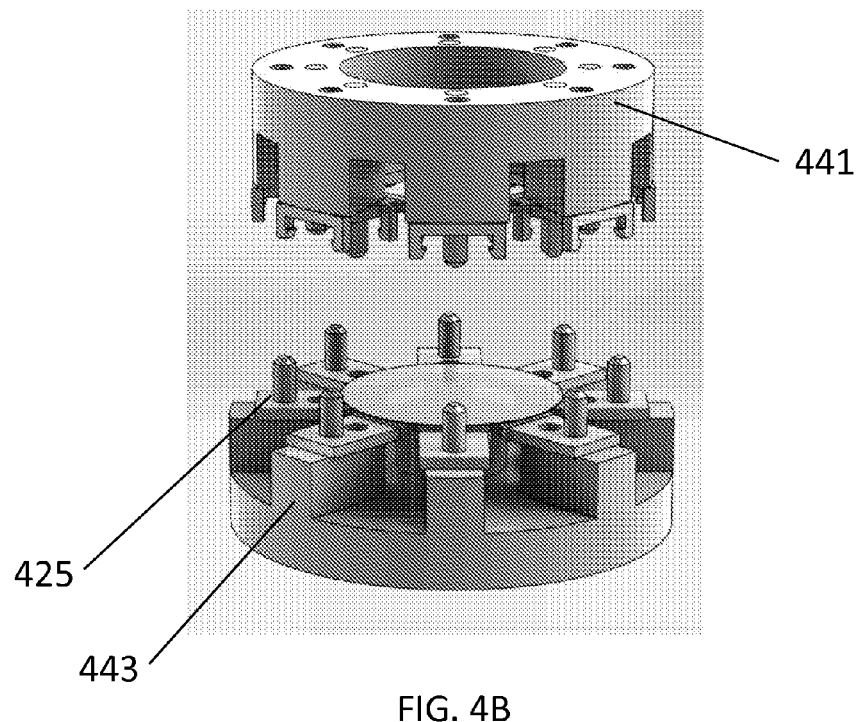
FIG. 4B illustrates clipping of top and bottom clamp portions using insertable stages in accordance with embodiments of the present disclosure.

FIG. 4A illustrates an insertable stage 443 with bottom clamp portions 425 and an insertable top clamp holder 441 with top clamp portions 426. Both top clamp portions and bottom clamp portions can have dowel pin holes 482 and dowel pins 484 for connection in addition to the clipping elements. FIG. 4B illustrates clipping of top and bottom clamp portions using an insertable stage 443 and a top clamp holder 441. The top clamp holder 441 with top clamp portions is lowered to fit the insertable stage 443 with bottom clamp portions.

Figure 5:
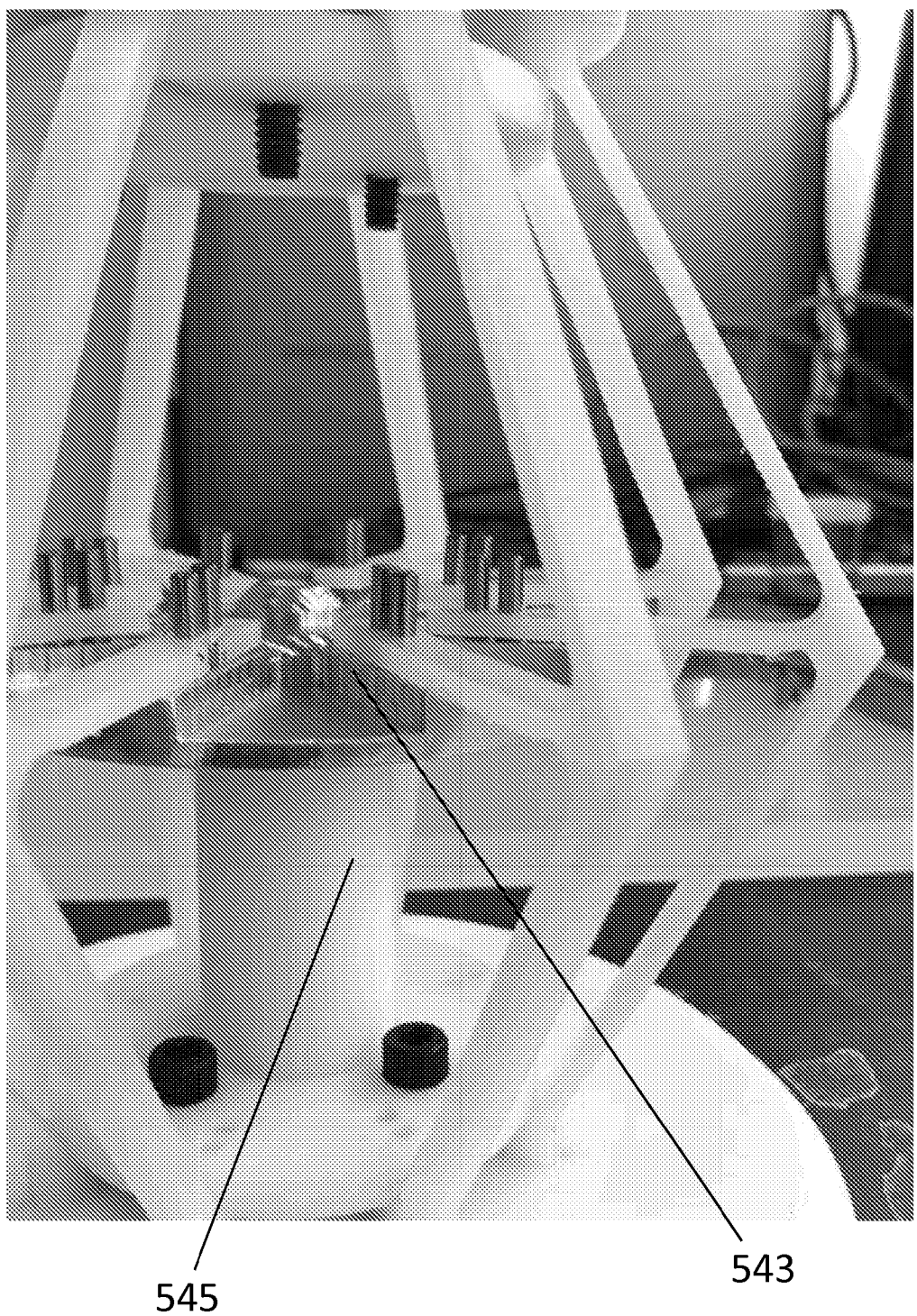
FIG. 5 illustrates an insertable stage and a positioning column in accordance with embodiments of the present disclosure.

An insertable stage can aid moving a sample membrane into the stretcher without damaging the membrane. In FIG. 5, a positioning column 545 can be inserted through a hole in the bottom plates that can be used to raise an insertable stage 543. The insertable stage 543 is raised to the level of the arms to align the arms using dowel pin holes. The insertable stage can also aid placing and clamping a membrane. After raising the insertable stage with the bottom clamp portions, a membrane can be placed on top of the bottom clamp portions. Then, the top clamp portions can be attached to the bottom clamp portions. Once the process is complete, the positioning column and the insertable stage can be lowered and removed.

Figure 6:
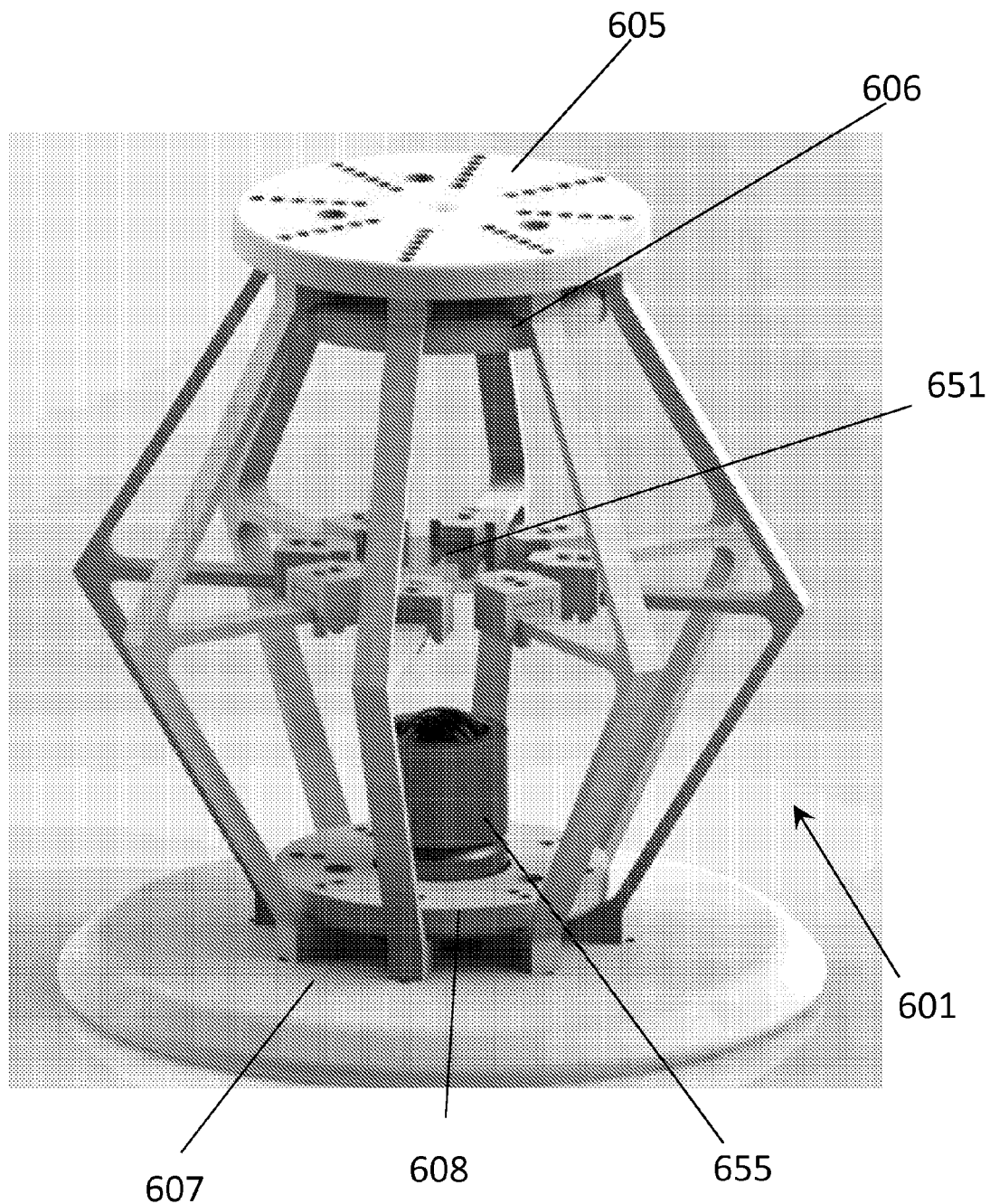
FIG. 6 illustrates an equi-biaxial stretcher with swappable secondary plates and a microscope in accordance with embodiments of the present disclosure.

FIG. 6 shows an equi-biaxial stretcher 601. A top plate 605 and a bottom plate 607 have eight sets of six linearly placed dowel pin holes. Each set of dowel pin holes are used by each truss and the dowel pin holes within a set can allow various positioning of trusses. For example, the trusses can be connected near the center of the plates or farther away from the center. If the trusses are connected to the top and bottom plates using two dowel pins, there are five configurations for placing the trusses. Then, a secondary top plate 606 and a secondary bottom plate 608 can be connected to the trusses. For a better fit and hold, the secondary plates can be swappable. When the trusses are positioned near the center of the plates, smaller secondary plates can be used. Similarly, when the trusses are positioned near the edge of the plates, larger secondary plates can be used.

Some exemplary diameters for the secondary plates are 0.9", 1.2", 1.5", 1.8", and 2.1." The sizes of membranes can vary slightly and still be clamped rigidly. Also, the equi-biaxial stretcher is fully scalable. Both the top and bottom plates and the secondary plates can be made with different sizes depending on the membrane size. The trusses can also be made in various sizes and structures and various inclining angles of the trusses from the vertical.

The bottom plate 607 and the secondary bottom plate 608 can have a hole in the middle. The hole is designed for inserting a microscope 655 to observe a membrane 651 as it gets stretched. An exemplary microscope 655 can be an optical microscope.

To use the system, one can cut a sample to size, assemble the stretcher with the corresponding plates, insert the insertable stage, clamp the sample on each arm, and remove the stage. Then, vertical force can be applied that results in stretching the sample membrane. Using a microscope, the sample can be observed and analyzed.

Figure 7:
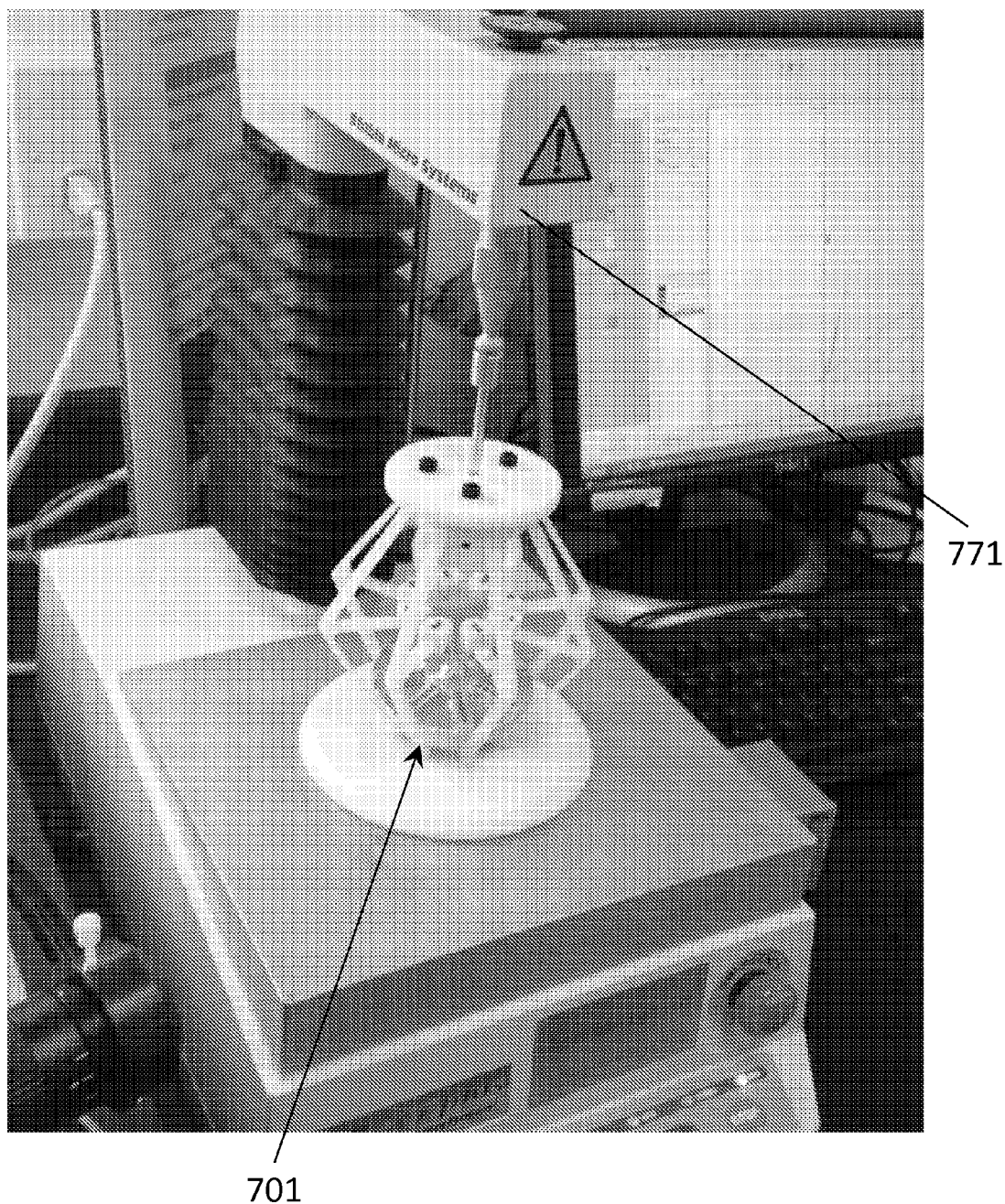
FIG. 7 illustrates force being applied to an equi-biaxial stretcher in accordance with embodiments of the present disclosure.

FIG. 7 shows an equi-biaxial stretcher 701 receiving downward force by a mechanical device 771. An exemplary mechanical device 771 is TA.XT Plus Texture Analyzer (TA.XT). The device uses a load cell to apply vertical force to the top plate and measures the vertical distance traveled by the top plate. Other devices capable of applying consistent force can work.

Beam Theory for Deflection

The deflection of the trusses and thus the stretch of a membrane can be determined based on a beam theory. Known material properties can be used to determine the amount of deflection for many different materials at a variety of connection angles. Displacement and angle of deflection of the beam can be found using Equations 1 and 2 respectively. Equation 3 can be used to determine the horizontal displacement of the middle arm of the beam, which is the same displacement each clamped portion of a sample will experience.

$$\delta = \frac{FL^3}{3EI} \qquad \text{Eq. 1}$$

$$\phi_B = \frac{FL^2}{2EI} \qquad \text{Eq. 2}$$

$$\delta_x = \delta \cos\theta \qquad \text{Eq. 3}$$

In these equations, $\delta$ is the displacement, $\phi$ is the angle of deflection, F is the force applied, E is the elastic modulus, L is the length of the beam, I is the moment of inertia, and $\theta$ is the angle of the beam to the horizon.

With the displacement and deflection of the beams accounted for, an accurate calculation of how the vertical force from the load cell translates to the horizontal forces on the sample can be determined. Beam theory can be used because it is linear in nature and simplifies calculations. Equation 4 calculates the critical load ($P_{Cr}$) of a beam, that is the amount of force that can cause a beam to fail and deform plastically.

$$P_{cr} = \frac{\pi^2 EI}{L^2} \qquad \text{Eq. 4}$$

For the testing of the beams of stretcher, the beams are press-fit between two aluminum plates to keep them from buckling while they are being compressed. The top and bottom portions of the beam are parallel to each other and are held in alignment along a vertical axis to ensure that the beam does not begin to curl inward. The top portion of the beam is held in place by dowel pins which insert into an aluminum slide designed to fit on top of the fixture and push one or two beams downward. Force is applied to the slide by the load cell attached to the TA.XT that will be used in experimentation with the final design and is controlled by a computer so the exact force applied can be programmed to a precise value. The displacement of the beam in the horizontal direction can be measured using a high resolution camera. As the beam is compressed, the 3 part intersection can move away from the test fixture and the camera can record how far the beam has moved. For example, a camera can measure with a precision of 100 microns. Using data collected from the force applied and the displacement of the beams, a curve can be made showing the relationship between the two. This curve can be used in the future by lab researchers to get the desired displacement by applying the correlating load.

Several beam lengths are analyzed to determine which length could achieve 20% deflection without reaching critical loading and while staying within the upper limit of the load cell attached to the universal testing machine (TA.XT). The different lengths investigated are: 1.1×, 1.25×, 1.4×, and 1.5× the original beam leg length of 1.56". The calculations for these various beam lengths can be seen in Table 4. From these calculations UHMW with a beam leg length equal to 1.4× the original length (1.56"×1.4=2.184") and with I3 moment of inertia was chosen as shown in Table 5. The required deflection (20%) is found by varying the applied force. Table 4 a shows the range of forces immediately surrounding the required deflection (0.15").

TABLE 1

Displacements determined from Eq. 1 for the selected materials at 1 lb and 5 lbs

| Common non-corrosive materials | Deflection for I1 (1 lb) | Deflection for I2 (1 lb) | Deflection for I3 (1 lb) | Deflection for I4 (1 lb) | Deflection for I5 (1 lb) |
|---|---|---|---|---|---|
| Delrin | 3.21E−04 | 6.43E−04 | 6.18E−02 | 1.75E−02 | 5.14E−03 |
| UHMW | 1.34E−03 | 2.68E−03 | 2.57E−01 | 7.27E−02 | 2.14E−02 |
| HDPE | 1.18E−03 | 2.35E−03 | 2.26E−01 | 6.40E−02 | 1.88E−02 |
| Common non-corrosive materials | Deflection for I1 (5 lb) | Deflection for I2 (5 lb) | Deflection for I3 (5 lb) | Deflection for I4 (5 lb) | Deflection for I5 (5 lb) |
| Delrin | 1.61E−03 | 3.21E−03 | 3.09E−01 | 8.73E−02 | 2.57E−02 |
| UHMW | 6.70E−03 | 1.34E−02 | 1.29E+00 | 3.64E−01 | 1.07E−01 |
| HDPE | 5.89E−03 | 1.18E−02 | 1.13E+00 | 3.20E−01 | 9.42E−02 |

TABLE 2

Angle of displacement determined from Eq. 2 for the selected materials at 1 lb and 5 lbs

| Common non-corrosive materials | Angle for I1 (1 lb) | Angle for I2 (1 lb) | Angle for I3 (1 lb) | Angle for I4 (1 lb) | Angle for I5 (1 lb) |
|---|---|---|---|---|---|
| Delrin | 3.09E−04 | 6.18E−04 | 5.94E−02 | 1.68E−02 | 4.95E−03 |
| UHMW | 1.29E−03 | 2.58E−03 | 2.48E−01 | 7.00E−02 | 2.06E−02 |
| HDPE | 1.13E−03 | 2.27E−03 | 2.18E−01 | 6.15E−02 | 1.81E−02 |
| Common non-corrosive materials | Angle for I1 (5 lb) | Angle for I2 (5 lb) | Angle for I3 (5 lb) | Angle for I4 (5 lb) | Angle for I5 (5 lb) |
| Delrin | 3.09E−04 | 3.09E−03 | 2.97E−01 | 8.40E−02 | 2.47E−02 |
| UHMW | 1.29E−03 | 1.29E−02 | 1.24E+00 | 3.50E−01 | 1.03E−01 |
| HDPE | 1.13E−03 | 1.13E−02 | 1.09E+00 | 3.08E−01 | 9.06E−02 |

TABLE 3

X component of displacement is shown by using values from above and Eq. 3 for the specified materials at 1 lb and 5 lbs

| Common non-corrosive materials | X Displacement for 11 (1 lb) | X Displacement for 12 (1 lb) | X Displacement for 13 (1 lb) | X Displacement for 14 (1 lb) | X Displacement for 15 (1 lb) |
|---|---|---|---|---|---|
| Delrin | 3.21E−04 | 6.43E−04 | 6.17E−02 | 1.75E−02 | 5.14E−03 |
| UHMW | 1.34E−03 | 2.68E−03 | 2.50E−01 | 7.26E−02 | 2.14E−02 |
| HDPE | 1.18E−03 | 2.35E−03 | 2.21E−01 | 6.38E−02 | 1.88E−02 |

| Common non-corrosive materials | X Displacement for 11 (5 lb) | X Displacement for 12 (5 lb) | X Displacement for 13 (5 lb) | X Displacement for 14 (5 lb) | X Displacement for 15 (5 lb) |
|---|---|---|---|---|---|
| Delrin | 1.61E−03 | 3.21E−03 | 2.95E−01 | 8.70E−02 | 2.57E−02 |
| UHMW | 6.70E−03 | 1.34E−02 | 4.20E−01 | 3.42E−01 | 1.07E−01 |
| HDPE | 5.89E−03 | 1.18E−02 | 5.25E−01 | 3.05E−01 | 9.38E−02 |

TABLE 4

Critical loads calculated with Eq. 4 for the specified materials at 1 lb

| Common non-corrosive materials | Critical Load for 11 | Critical Load for 12 | Critical Load for 13 | Critical Load for 14 | Critical Load for 15 |
|---|---|---|---|---|---|
| Delrin | 4.08E+03 | 2.04E+03 | 2.12E+01 | 7.52E+01 | 2.55E+02 |
| UHMW | 9.80E+02 | 4.90E+02 | 5.10E+00 | 1.80E+01 | 6.13E+01 |
| HDPE | 1.11E+03 | 5.57E+02 | 5.80E+00 | 2.05E+01 | 6.97E+01 |

TABLE 5

Required force to deflect a beam length 1.4 × the length of the original L × 1.4 for UHMW to find deflection x

| Load | Deflection | Angle | X Dis | X Dis Full Sys |
|---|---|---|---|---|
| 1.5 | 2.45 | 1.12 | 1.06 | 6.65E−02 |
| 1.6 | 2.61 | 1.20 | 0.96 | 5.98E−02 |
| 1.7 | 2.77 | 1.27 | 0.82 | 5.13E−02 |
| 1.8 | 2.94 | 1.35 | 0.66 | 4.11E−02 |
| 1.9 | 3.10 | 1.42 | 0.47 | 2.91E−02 |
| 2.0 | 3.26 | 1.49 | 0.25 | 1.55E−02 |
| 2.1 | 3.43 | 1.57 | 0.01 | 3.35E−04 |
| 2.2 | 3.59 | 1.64 | 0.26 | 1.64E−02 |
| 2.3 | 3.75 | 1.72 | 0.55 | 3.45E−02 |
| 2.4 | 3.91 | 1.79 | 0.86 | 5.40E−02 |
| 2.5 | 4.08 | 1.87 | 1.19 | 7.47E−02 |
| 2.6 | 4.24 | 1.94 | 1.54 | 9.63E−02 |
| 2.7 | 4.40 | 2.02 | 1.9 | 1.19E−01 |
| 2.8 | 4.57 | 2.09 | 2.28 | 1.42E−01 |
| 2.9 | 4.73 | 2.17 | 2.66 | 1.66E−01 |
| 3.0 | 4.89 | 2.24 | 3.04 | 1.90E−01 |
| 3.1 | 5.06 | 2.32 | 3.43 | 2.14E−01 |

The thickness of each of the beam legs can play a pivotal role in the success of this device. As seen in Equation 5, the moment of inertia of the beam is largely dependent on the beam thickness. A small change in beam thickness can result in a significant change in displacement. This can happen because the displacement is inversely proportional to the moment of inertia of the beam. In Equation 5, I is the moment of inertia, b is the beam width, and h is the beam thickness.

$$I = \frac{bh^3}{12} \qquad \text{Eq. 5}$$

The effects of fatigue on the beam can also be considered. The number of cycles to fatigue is generally looked at as the amount of loading and unloading cycles that a beam of device can experience before critical failure. In this case, the number of cycles until permanent deformation is needed. Because no pretense for this work exists, 10% of the number of cycles until failure will be used as a baseline. Equation 6 shows the formulas for fatigue. In equation 6, N is the number of cycles until failure, $\sigma_{rev}$ is the completely reversed stress, f is the fatigue strength fraction, $S_{ut}$ is the minimum tensile strength, and $S_e$ is the endurance limit.

$$N = \left(\frac{\sigma_{rev}}{a}\right)^{\frac{1}{b}} \text{ where } a = \frac{(fS_{ut})^2}{S_e} \text{ and } b = -\frac{1}{3}\log\left(\frac{fS_{ut}}{S_e}\right) \qquad \text{Eq. 6}$$

The angle between the two legs 215 can be 90°, but other angles, such as 120°, are possible. Each beam will be aligned such that the stretching plane cuts the 90° beam into two 45° sections. Equations 1 and 2 can be used to find the maximum displacement of each beam individually. Using these results and the properties of several commercially available materials, the amount of force required to achieve the desired beam deflection can be determined. Once the amount of force required to deflect one beam to the desired amount is determined, that data can be extrapolated to find the amount of force required to bend all 8 beams to the desired deflection.

If the system is too rigid, it may require too much force to achieve nominal deflection. On the other hand, if the system is too compliant, it may not survive repeated usage. Some potential materials and their elastic moduli can be seen below in Table 6. (See "Interstate Plastics—Materials." Interstate Plastics. Web. Retrieved on 12 Jan. 2012. Retrieved from the Internet: <URL: http://www.interstateplastics.com/materials.php>).

TABLE 6

Corrosion Resistant Materials and Elastic Moduli

| Common non-corrosive materials | E Modulus (psi) |
|---|---|
| Delrin | 4.25E+05 |
| UHMW | 9.00E+04 |
| Nylon 6/6 | 3.13E+05 |
| Nylon 6/12 | 3.00E+05 |

TABLE 6-continued

Corrosion Resistant Materials and Elastic Moduli

| Common non-corrosive materials | E Modulus (psi) |
|---|---|
| Teflon | 1.00E+05 |
| PEEK | 5.80E+05 |
| PE | 1.70E+05 |

These materials possess some desirable characteristics. They are corrosion resistant, some are wear resistant, and their elastic moduli are in the same general range. Several potential beam cross-sections and the amount of displacement 20% deflection causes are defined below in.

TABLE 7

Exemplary Constants
Constants

| L | 2.03E+00 (in) |
|---|---|
| $I_1$ (2 cm × 1 cm) | 4.00E−03 (lbin$^2$) |
| $I_2$ (1 cm × cm) | 2.00E−03 (lbin$^2$) |
| $I_3$ (0.5 cm × 0.5 cm) | 1.25E−04 (lbin$^2$) |
| $I_4$ (r = 0.5 cm) | 7.37E−05 (lbin$^2$) |
| $I_5$ (1 cm × 0.5 cm) | 2.50E−04 (lbin$^2$) |
| Ideal Deflection (20%) | 1.12E−01 (in) |

Using Equations 1 and 2, the maximum displacement and slope of the beam can be determined and can then be broken down into x and y components. In this study the most important factor is the displacement in x, as the goal of the design is to achieve 20% beam deflection in the x direction. Equations 3 can be used to convert the maximum displacement and slope into its x component.

All the results from the beam theory calculations can be seen in Appendix A. In the results, it can be seen that most of the values are close to the desired x displacement. By varying the amount of force and the shape of the beam cross sections, any of the materials can be used in the design. The next step involved in the beam theory calculations can be used to settle on cross sections and length. After this point a beam material can be decided and the force required to deflect it to the desired amount can be determined.

Equation 6 can be used to calculate the number of cycles until the device failed. The values used for each of the variables are as follows: σrev=750 psi (max von Mises stress from FEA), f=0.9 (approximation), Sut=2600 psi, and Se=355.6 psi (from calculation, see Equation 7). The number of cycles is determined to be approximately 50,000. Based on the previous assumption that 10% of the over number of cycles will results in plastic deformation, it has been determined that the device can withstand 5,000 loading and unloading cycles before any beams need to be replaced.

The variables shown in Equation 7 are as follows: ka is the surface modification factor (0.366), kb is the size modification factor (1), kc is the load modification factor (1), kd is the temperature modification factor (1), ke is the reliability factor (0.814), and kf is the miscellaneous effects factor (1).

$$S_e = 0.5 S_{ut} k_a k_b k_c k_d k_e k_f \qquad \text{Eq. 7}$$

Additional calculations can be performed to determine if a change in thickness of the beams affected the expected displacement of the beams. Equations 1, 2, and 3 can be used to determine this. Table 8 depicts how a small (5-10%) increase or decrease in beam thickness significantly affects the expected displacement. These calculations reiterate the importance for very precise machining techniques.

TABLE 8

Effect of Thickness
Effects of Change in Thickness

| Change in Moment of Inertia | | Deflection | Angle | X Displacement | % Change from Spec |
|---|---|---|---|---|---|
| 0% | I | 2.083E−05 | 1.689E−01 | 1.16E−01 | 0.17 | 0.00% |
| +5% | $I_1$ | 2.412E−05 | 1.46E−01 | 1.00E−01 | 0.15 | −14.62% |
| −5% | $I_2$ | 1.786E−05 | 1.97E−01 | 1.36E−01 | 0.20 | 14.81% |
| +10% | $I_3$ | 2.773E−05 | 1.27E−01 | 8.73E−02 | 0.13 | −25.65% |
| −10% | $I_4$ | 1.519E−05 | 2.32E−01 | 1.59E−01 | 0.23 | 34.55% |

Testing Methods

An exemplary testing method for single and double beams is provided below.

1. Start testing at force amount calculated in Beam Theory Calculations (0.35625 lbs) for a single beam
   a. Repeat 20×
   b. Record Results using camera setup (displacement test)
   c. Find average displacement at this weight
   d. Compile Force vs. Displacement Curves
2. Test based on force required in FEA (0.5375 lbs) for a single beam
   a. Repeat 20×
   b. Record Results using camera setup (displacement test)
   c. Find average displacement at this weight
   d. Compile Force vs. Displacement Curves
3. Assess closeness to desired deflection
   a. increase/decrease load by 10% and repeat 20× at that load
   b. Record Results using camera setup (displacement test)
   c. Find average displacement at this weight
   d. Compile Force vs. Displacement Curves
   e. Do this until desired deflection is found
4. Using force found between steps 1, 2, & 3, resume testing for double beam setup.
   a. Double force found in step 3
   b. Repeat 20×
   c. Record Results using camera set up (displacement test)
   d. Find average displacement at this amount of force
   e. Compile Force vs. Displacement Curves
   f. Compare with force required for single beam
   g. Assess linearity of scaling test from single beam setup to double beam setup 5. Lifecycle Testing
   a. Set up strain gauges in configuration shown
   b. Use force value found for desired displacement (20%)
   c. Repeat test until beam failure (at least 100×)
   d. Failure is defined as a decrease in required force by a factor of more than 5%, fracture of beam, or observed degradation of performance
6. If force falls within limits of available load cell, begin machining and assembling prototype.

Figure 8A:
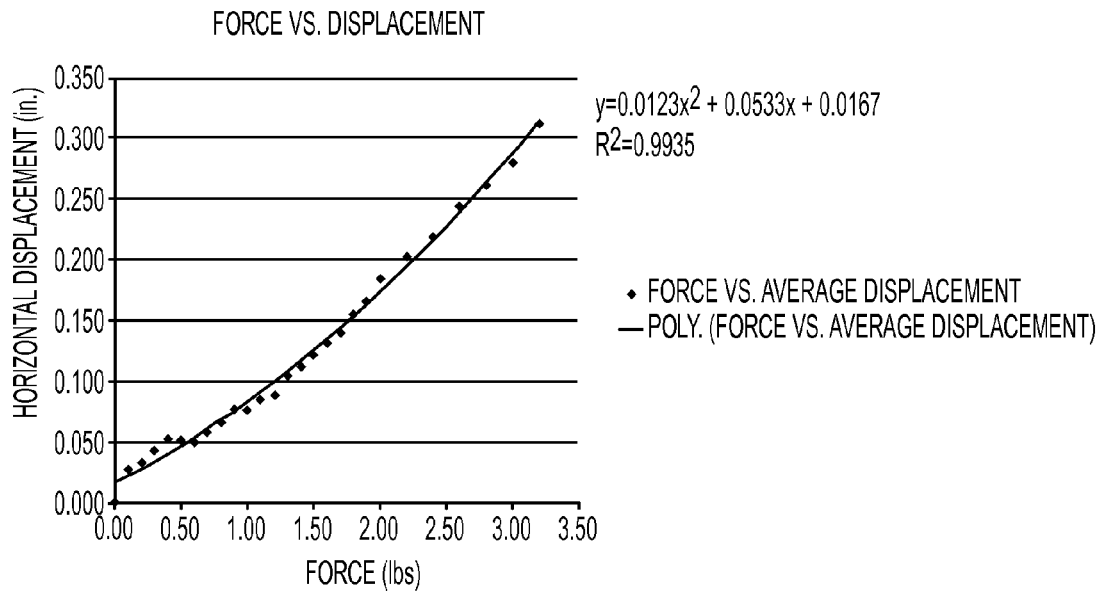
FIG. 8A illustrates an exemplary force and displacement curve in accordance with embodiments of the present disclosure.

An exemplary testing method for the full system is provided below.
1. Pretesting requirements
   a. Set up camera and load cell in Biomechanics Lab (243 Forsythe)
   b. Draw vertical line in marker on arm of beam
   c. Set focus to begin testing
   d. Prototype must be built and functional
2. Start testing at force amount found during single and double beam testing (6.16 lbs). This test is being done to verify that the approximated amount of force will be sufficient to deflect the system 20% in the lateral direction
   a. Create scale for measurements (This will be a background, behind the beam being measured with various lines on it to use as reference)
   b. Record before picture
   c. Start load cell and wait until beam settles, then take after picture
   d. Use Image J software
      i. Set Scale by drawing vertical line from top edge of beam arm to bottom edge, then assigning value of 0.1"
      ii. Take measurement by drawing line from edge of vertical line (drawn at beginning of test), and selecting take measurement
   e. Increase/decrease load by 10% and repeat steps ac until the proper deflection is found
   f. Repeat 50×
   g. Find average displacement at his weight
   h. A second user should verify results by taking measurement a second time, human error can be present in the Image J software and will be minimized by repeating measurement with a different user
3. This test will be done in increments of the load in previous test
   a. Using same scale as previous test
   b. Split load into 20 increments
   c. Take before picture
   d. Start load cell with first increment as max load
   e. Take after picture
   f. Use Image J software
      i. Set scale by drawing vertical line from top edge of beam arm to bottom edge, then assigning value of 0.1"
      ii. Take measurement by drawing line from edge of vertical line (drawn at beginning of test), and selecting take measurement
   g. Repeat 20×
   h. Find average displacement at this weight
   i. A second user should verify results by taking measurement a second time, human error can be present in the Image J software and will be minimized by repeating measurement with a different user
   j. Increment the load and repeat steps c-I, until the load found in Test 1 is achieved All the displacement values can be put into a graph as shown in FIG. 8A: this graph can become the displacement curve for this device. We can have 20 data points at 20 equal increments of force. From this we can compile our final Force vs. Horizontal Displacement curve. The load cell can also provide the amount of vertical displacement that is achieved from that force. We can use this data, in tandem, with the horizontal displacement data to compile our Vertical Displacement vs. Horizontal Displacement curve.

The steps for preparing sample and loading into an equi-biaxial stretcher is provided.
1. Pretesting requirements
   a. Set up camera and load cell in Biomechanics Lab (243 Forsythe)
   b. Set focus and take picture of sample before testing
   c. Prepare sample and load into Equibiaxial stretcher
2. Test with force found from full Prototype Displacement Testing
   a. Start load cell and wait until max force is achieved
   b. Hold for 1 minute
   c. Release force on device
   d. Remove device from load cell
   e. Remove sample from device
   f. Take second picture of sample
   g. Compare to previous picture to assess damage
   h. If damage is minimal, proceed to next test
   i. Repeat steps a-h, until 100 tests is reached
3. If another iteration of clip exists, repeat test 1 (described above)

The clips can be designed to apply the proper amount of force to the sample without damaging its integrity. Visual verification can be a mean to assess the damage being caused. An equi-biaxial stretcher can be made to withstand 100 testing cycles before any significant damage is done. Several iterations of clips exist at this point. During the testing, design can be altered for causing the least damage to the samples (e.g., hydro gel sheets and pig lenses).

Figure 8B:
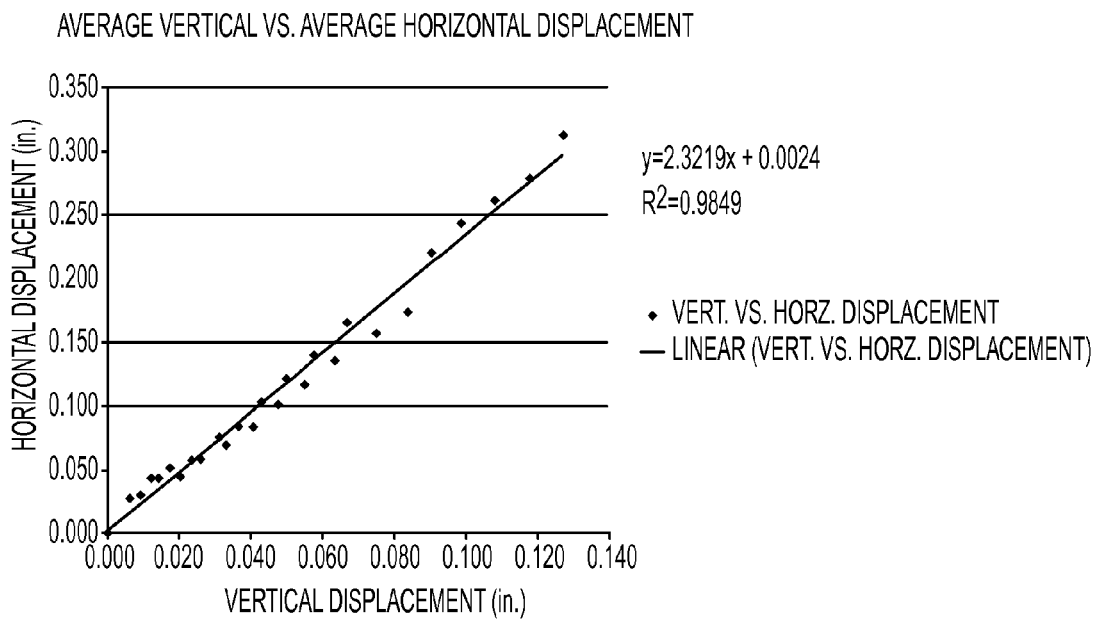
FIG. 8B illustrates an exemplary horizontal and vertical displacement curve in accordance with embodiments of the present disclosure.

Some of the testing results of the equi-biaxial stretcher is provided. The device can operate within an accurate enough range of motion to be useful to the biomedical community. Curves showing the expected displacement as function of both known vertical displacement and known vertical force can be seen in FIGS. 8A and 8B. FIG. 8A shows the amount of displacement expected from applying a known compression force to the top plate of the device while no sample is loaded. FIG. 8B shows the expected displacement caused by a known vertical displacement that is applied to the top plate of the device.

As will be apparent to one of ordinary skill in the art from a reading of this disclosure, the present disclosure can be embodied in forms other than those specifically disclosed above. The particular embodiments described above are, therefore, to be considered as illustrative and not restrictive. Those skilled in the art will recognize, or be able to ascertain, using no more than routine experimentation, numerous equivalents to the specific embodiments described herein. The scope of the invention is as set forth in the appended claims and equivalents thereof, rather than being limited to the examples contained in the foregoing description.

What is claimed is:
1. A system for stretching a membrane, the system comprising:
   a first main plate configured to receive force perpendicular to a surface of the first main plate and move perpendicular to the surface;

a second main plate substantially in parallel with the first main plate;

a plurality of trusses evenly distributed in circle, each truss comprising at least two legs and an arm, wherein:
the at least two legs and the arm meet at a center of their corresponding truss, wherein the two legs meet at a first angle less than 180 degrees;
a first leg of the at least two legs of each truss is coupled to the first main plate;
a second leg of the at least two legs of each truss is coupled to the second main plate;
the arm of each truss points in a radially inward direction; and
the center of each truss points in a radially outward direction;

a plurality of clamps, each clamp coupled to an end of a corresponding arm of a truss in the plurality of trusses for clamping a membrane and;

an insertable stage and a positioning column configured to lift the insertable stage;

wherein moving the first main plate towards the second main plate causes the plurality of trusses to bend such that the at least two legs of each truss meet at a second angle less than the first angle to stretch the clamped membrane.

2. The system of claim 1, wherein the moving the first main plate towards the second main plate exerts substantially equal force to the plurality of trusses to displace each of the plurality of arms and each of the plurality of clamps in a radially outward direction.

3. The system of claim 1, further comprising:
a first secondary plate for fixing the first legs of the plurality of trusses between the first main plate and the first secondary plate; and
a second secondary plate for fixing the second legs of the plurality of trusses between the second main plate and the second secondary plate.

4. The system of claim 3, wherein the first and second secondary plates are swappable.

5. The system of claim 1, wherein each arm bisects an angle between the first and second legs of its corresponding truss, and wherein the plurality of arms are substantially parallel with the first and second main plates.

6. The system of claim 1, wherein each clamp of the plurality of clamps comprises a top clamp portion and a bottom clamp portion, the top clamp portion and the bottom clamp portion being separable.

7. The system of claim 1, wherein the plurality of trusses comprise at least eight trusses and the plurality of clamps comprise at least eight clamps.

8. The system of claim 1, wherein the plurality of trusses comprise at least one of polymers or metals.

9. The system of claim 1, wherein the plurality of trusses are made by 3D printing.

10. The system of claim 1, wherein the plurality of trusses are made by injection molding.

11. The system of claim 1, wherein the plurality of trusses comprise a non-corrosive material.

12. The system of claim 11, wherein the non-corrosive material comprises at least one of Delrin, UHMW, Nylon 6/6, Nylon 6/12, Teflon, PEEK, and PE.

13. A method of stretching a membrane using a membrane stretcher, the method comprising:
providing a membrane;
clamping a membrane with the plurality of clamps of the system of claim 1; and
applying force substantially perpendicular to the first main plate for stretching the membrane.

14. A method of using a membrane stretcher, the method comprising:
inserting an insertable stage into the system of claim 6;
raising the insertable stage to substantially level with the plurality of arms;
placing the bottom clamp portions of the plurality of clamps on the insertable stage;
placing a membrane on the bottom clamp portions;
attaching the top clamp portions of the plurality of clamps to the bottom clamp portions; and
lowering the insertable stage.

15. The method of claim 14, wherein the top clamp portions are placed on a top clamp holder and wherein the attaching the top clamp portions comprises lowering the top clamp holder.

16. The method of claim 14, further comprising applying force substantially perpendicular to the first main plate for stretching the membrane.

17. The method of claim 14, wherein the insertable stage is raised with a positioning column inserted through a hole in the second main plate.

18. The method of claim 14, further comprising aligning the plurality of arms with the insertable stage.

19. The system of claim 14, further comprising inserting a microscope to observe the membrane.

* * * * *